(12) United States Patent
Fujii

(10) Patent No.: US 10,244,932 B2
(45) Date of Patent: Apr. 2, 2019

(54) ENDOSCOPE SYSTEM WITH ANTIFOGGING HEATING OF DISTAL LENS

(71) Applicant: OLYMPUS CORPORATION, Tokyo (JP)

(72) Inventor: Toshiyuki Fujii, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 14 days.

(21) Appl. No.: 15/669,235

(22) Filed: Aug. 4, 2017

(65) Prior Publication Data

US 2017/0332894 A1 Nov. 23, 2017

Related U.S. Application Data

(63) Continuation of application No. 15/089,695, filed on Apr. 4, 2016, now abandoned, which is a continuation (Continued)

(30) Foreign Application Priority Data

Dec. 18, 2013 (JP) .................. 2013-261361

(51) Int. Cl.
*A61B 1/00* (2006.01)
*A61B 1/05* (2006.01)
(Continued)

(52) U.S. Cl.
CPC ............ *A61B 1/127* (2013.01); *A61B 1/0019* (2013.01); *A61B 1/00096* (2013.01);
(Continued)

(58) Field of Classification Search
CPC ..... A61B 1/00158; A61B 1/0016; A61B 1/04; A61B 1/00071; A61B 1/0008; A61B 1/00096; A61B 1/00105; A61B 1/00188
(Continued)

(56) References Cited

U.S. PATENT DOCUMENTS 5,531,664 A * 7/1996 Adachi ................ A61B 1/0058
600/149
7,429,808 B2 9/2008 Lehr et al.
(Continued)

FOREIGN PATENT DOCUMENTS

EP 2175458 A2 4/2010
JP 2004-325603 A 11/2004
(Continued)

OTHER PUBLICATIONS

International Search Report dated Mar. 17, 2015 issued in PCT/JP2014/082952.
(Continued)

*Primary Examiner* — John P Leubecker
*Assistant Examiner* — William B Chou
(74) *Attorney, Agent, or Firm* — Scully, Scott, Murphy & Presser, P.C.

(57) ABSTRACT

An endoscope includes: a first lens located at a distal-most position, a part of the first lens being exposed outside; a movable lens barrel configured to be able to move, and configured to hold a movable lens disposed on a proximal end side with respect to the first lens; an actuator unit including a coil that drives the movable lens barrel and generates heat by receiving a supply of electric power; and a control section that outputs first electric power to the coil when holding the movable lens barrel at a predetermined position, and outputs second electric power larger than the first electric power to the coil when conducting heat generated from the coil to the first lens at the predetermined position.

4 Claims, 11 Drawing Sheets

Related U.S. Application Data of application No. PCT/JP2014/082952, filed on Dec. 12, 2014.

(51) Int. Cl.
*A61B 1/12* (2006.01)
*G02B 23/24* (2006.01)

(52) U.S. Cl.
CPC ...... *A61B 1/00163* (2013.01); *A61B 1/00188* (2013.01); *A61B 1/05* (2013.01); *G02B 23/2438* (2013.01); *A61B 1/00006* (2013.01); *A61B 1/00066* (2013.01); *A61B 1/128* (2013.01); *G02B 23/2469* (2013.01)

(58) Field of Classification Search
USPC ....... 600/109, 110, 118, 121, 127, 129, 130, 600/133, 140, 151, 160, 169, 172, 175, 600/176
See application file for complete search history.

(56) References Cited

U.S. PATENT DOCUMENTS

| | | | |
|---|---|---|---|
| 8,264,104 B2 | 9/2012 | Schrader | |
| 8,278,785 B2 | 10/2012 | Schrader et al. | |
| 8,946,947 B2 | 2/2015 | Kelp | |
| 9,385,580 B2 | 7/2016 | Wieters et al. | |
| 2004/0223074 A1 | 11/2004 | Takada | |
| 2007/0083084 A1* | 4/2007 | Esashi | A61B 1/0051 600/146 |
| 2007/0149856 A1 | 6/2007 | Segawa | |
| 2008/0297922 A1* | 12/2008 | Lule | G02B 7/08 359/824 |
| 2009/0124856 A1* | 5/2009 | Otawara | A61B 1/00091 600/129 |
| 2010/0127580 A1 | 5/2010 | Schrader | |
| 2010/0309553 A1 | 12/2010 | Nagamizu | |
| 2013/0197311 A1 | 8/2013 | Sherwin | |
| 2013/0314517 A1 | 11/2013 | Makiyama et al. | |
| 2014/0200406 A1 | 7/2014 | Bennett et al. | |
| 2014/0221743 A1 | 8/2014 | Sugiyama | |

FOREIGN PATENT DOCUMENTS

| | | | |
|---|---|---|---|
| JP | 2013-523372 A | 6/2013 | |
| JP | 5274733 B1 | 8/2013 | |
| WO | WO 2011/128894 A1 | 10/2011 | |
| WO | WO 2013/054787 A1 | 4/2013 | |

OTHER PUBLICATIONS

Japanese Office Action dated Sep. 8, 2015 issued in JP 2015-528751.

Office Action dated Sep. 30, 2016 received in U.S. Appl. No. 15/089,695.

Office Action dated Mar. 7, 2017 received in U.S. Appl. No. 15/089,695.

Extended Supplementary European Search Report dated Apr. 21, 2017 in European Patent Application No. 14 87 2139.2.

* cited by examiner

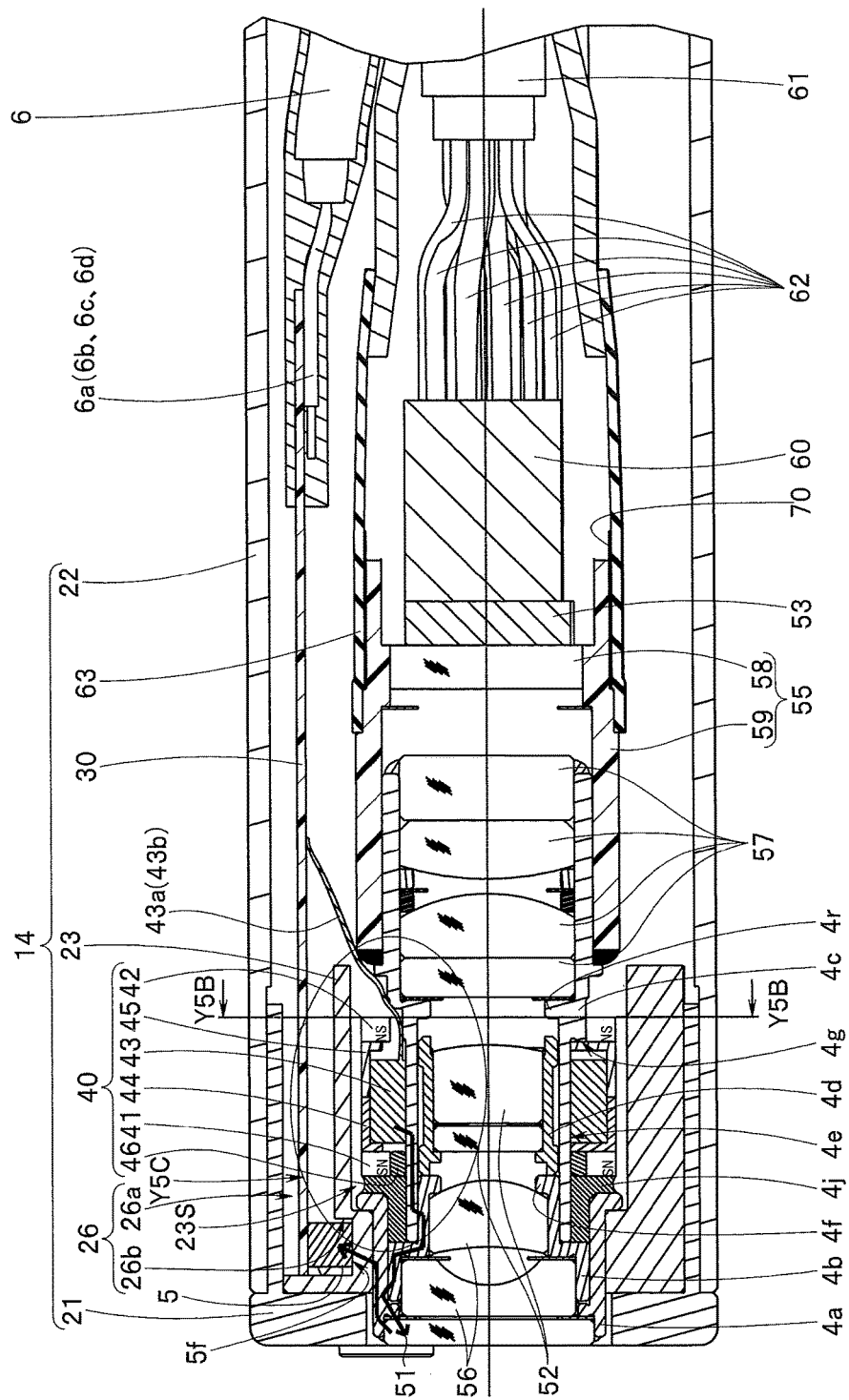

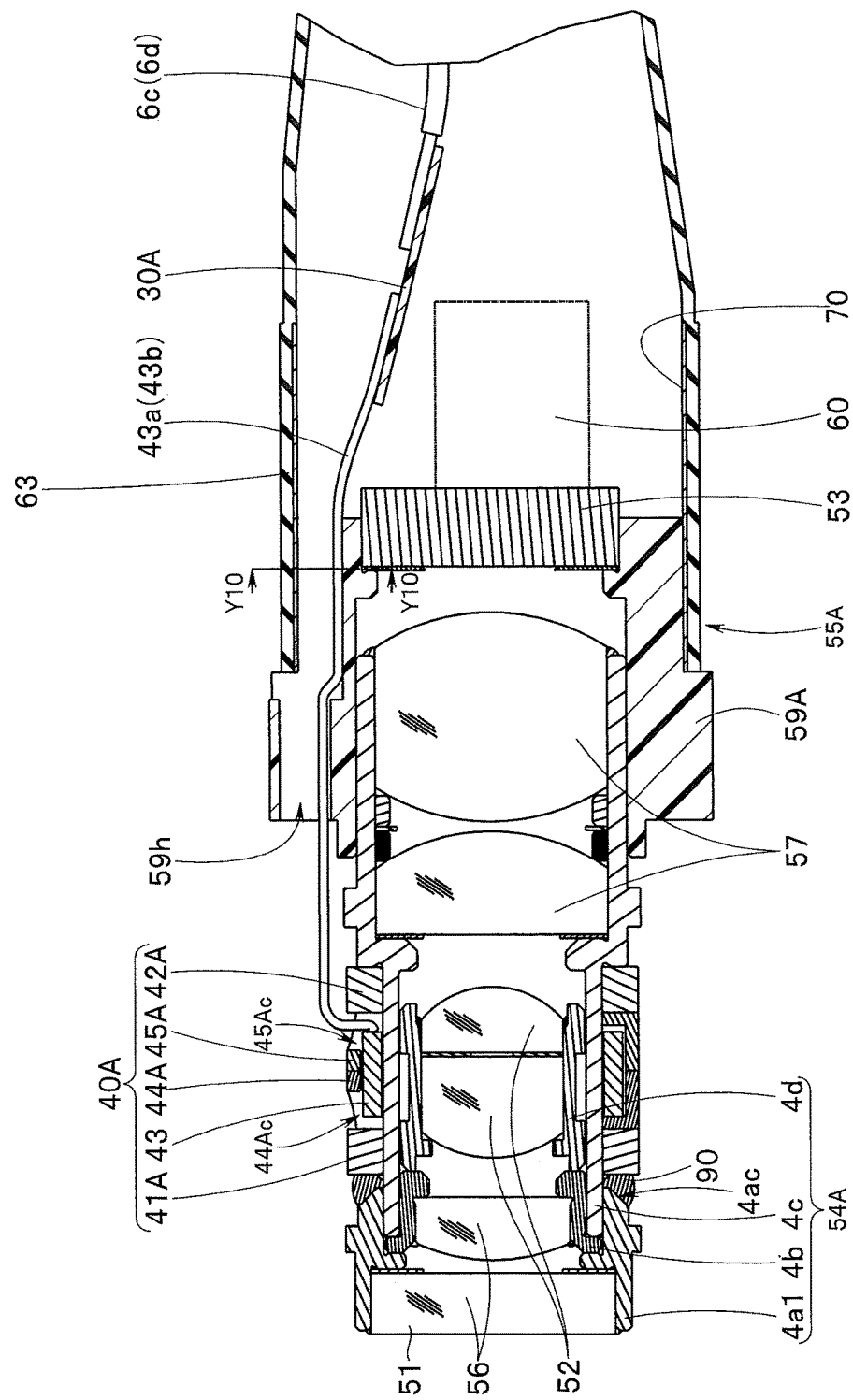

ENDOSCOPE SYSTEM WITH ANTIFOGGING HEATING OF DISTAL LENS

CROSS REFERENCE TO RELATED APPLICATION

This application is a continuation application of U.S. patent application Ser. No. 15/089,695 filed on Apr. 4, 2016, which is a continuation of PCT/JP2014/082952 filed on Dec. 12, 2014 and claims benefit of Japanese Application No. 2013-261361 filed in Japan on Dec. 18, 2013, the entire contents of each of which are incorporated herein by reference.

BACKGROUND OF THE INVENTION

1. Filed of the Invention

The present invention relates to an endoscope system that prevents fogging from occurring on a distal end lens.

2. Description of the Related Art

Endoscopes are used in medical fields, industrial fields, and the like. Such endoscopes include, what is called, an electronic endoscope (hereinafter shortly referred to as endoscope) which incorporates an image pickup unit at a distal end portion of an insertion portion.

In such an endoscope, there is a desire for an image pickup unit that is capable of changing optical characteristics such as focal depth, image-forming magnification, view angle, and the like, with respect to an object to be observed, depending on a site to be observed or a purpose of observation.

A body cavity into which an endoscope is inserted, for example, is under an environment in which the temperature is about 35 to 37 degrees Celsius, and the humidity is about 98 to 100%. In such an environment, when the insertion portion is inserted in the body cavity, moisture condensation and fogging are likely to occur on a surface of a distal end lens located on a distal end surface of the insertion portion, due to a difference between the temperature of an endoscopic examination room and the temperature in the body cavity.

Therefore, in endoscopic observation, it is desirable to use an endoscope that is capable of preventing occurrence of fogging which is likely to impede the observation, or capable of removing the occurred fogging.

For example, Japanese Patent Application Laid-Open Publication No. 2004-325603 discloses a technique of countermeasures against moisture condensation or freezing for a camera. According to such a technique, a film-shaped heater is circularly disposed in a region where the heater exerts no influence on an image pickup optical path so as to be sandwiched between a flat face of a front-face lens and a flat face of a second lens, and a temperature sensor that acquires a temperature in a lens module is provided on an inner wall surface of a lens holder, for example. The lens module is heated by electric power being supplied to the heater based on the output from the temperature sensor.

On the other hand, U.S. Pat. No. 8,264,104 discloses a motor for endoscope optical system in which a coil is excited with a current to cause a slider to be displaced from a holding position along a longitudinal direction. The motor includes two permanent magnets and a coil arranged between the two magnets.

Combining the technique of the motor for endoscope optical system disclosed in the U.S. Pat. No. 8,264,104 and the technique of the countermeasure against moisture condensation for camera disclosed in the Japanese Patent Application Laid-Open Publication No. 2004-325603 can provide an endoscope which is provided with an image pickup unit capable of changing optical characteristics and which is configured to be able to prevent occurrence of fogging on a surface of a distal end lens in an observation optical system of the endoscope or remove the fogging occurred on the surface of the distal end lens.

SUMMARY OF THE INVENTION

An endoscope system according to one aspect of the present invention includes: a first lens located at a distal-most position, a part of the first lens being exposed outside; a movable lens barrel configured to be able to move, and configured to hold a movable lens disposed on a proximal end side with respect to the first lens; an actuator unit including a coil that drives the movable lens barrel and generates heat by receiving a supply of electric power; and a control section that outputs first electric power to the coil when holding the movable lens barrel at a predetermined position, and outputs second electric power larger than the first electric power to the coil when conducting heat generated from the coil to the first lens at the predetermined position.

BRIEF DESCRIPTION OF THE DRAWINGS

FIG. 5A is a view for illustrating an actuator unit including both a driving mechanism and an anti-fogging function and is an enlarged cross-sectional view taken along arrow line Y5A-Y5A in FIG. 2.

FIG. 9 is a view for illustrating another exemplary configuration of an image pickup unit.

DETAILED DESCRIPTION OF THE PREFERRED EMBODIMENTS

Figure 1:
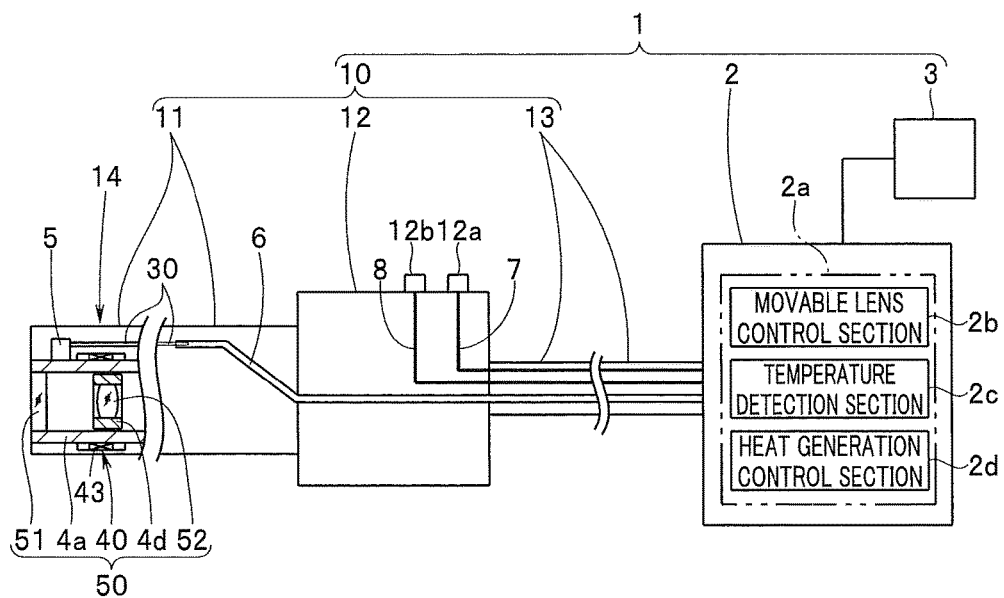
FIG. 1 is a view for illustrating an endoscope system mainly including an endoscope having a lens unit and a processor, according to the present invention.

Hereinafter, embodiments of the present invention will be described with reference to the drawings.

In the drawings to be referred to in the description below, there is a case where the scale size is made different for each of the components in order to allow each of the components to be illustrated in a recognizable size in the drawings. In addition, the present invention is not limited only to the number, the shapes, ratio of the sizes of the components, a relative positional relationship among the components, and the like as illustrated in the drawings.

With reference to FIGS. 1 to 7, description will be made on the configurations of a lens unit, an endoscope having the lens unit, and an endoscope system having the endoscope.

As shown in FIG. 1, an endoscope system 1 mainly includes an endoscope 10, a processor 2, and a display apparatus 3, for example.

The endoscope 10 includes an insertion portion 11, an operation portion 12, and a universal cord 13.

The insertion portion 11 includes, at a distal end side thereof, a distal end portion 14. A distal end lens 51 is arranged on a distal end surface of the distal end portion 14. The distal end lens 51 is a first lens of an image pickup unit 50 which is a lens unit. The distal end lens 51 has a distal end surface exposed outside of the endoscope 10, and is fixed to and held by a first objective lens barrel 4a.

The image pickup unit 50 includes a movable lens 52 configured to advance and retreat with respect to an optical axis direction for focusing or zooming. The movable lens 52 is fixed to and held by a movable lens barrel 4d. The movable lens barrel 4d is driven by an actuator unit 40 as lens driving means, to advance and retreat.

The actuator unit 40 is provided with a heat generation/driving dual-purpose coil (hereinafter shortly referred to as dual-purpose coil) 43 which serves both as heat generation means and lens driving means.

In the vicinity of the distal end lens 51 of the distal end portion 14, a thermistor 5 as temperature detection means is arranged. A flexible substrate 30 is extended from the thermistor 5 toward the proximal end side. As shown in FIG. 5A, a pair of wirings for sensor 6a, 6b and a pair of dual-purpose wirings 6c, 6d are connected to the proximal end of the flexible substrate 30.

Figure 3:
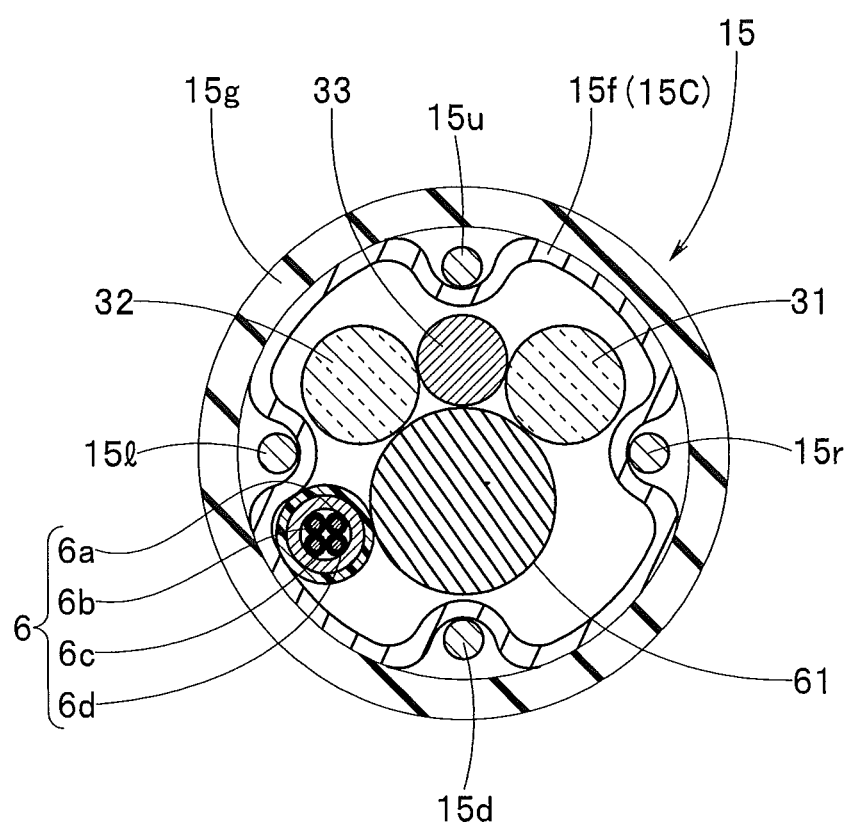
FIG. 3 is a view for illustrating a configuration of a distal end bending piece portion that configures a bending portion of the insertion portion and is a cross-sectional view taken along arrow line Y3-Y3 shown in FIG. 4.

As shown in FIG. 3, the wirings for sensor 6a, 6b and the dual-purpose wirings 6c, 6d are integrated as an actuator cable 6. The actuator cable 6 is inserted through the distal end portion 14 which configures the insertion portion 11, a bending portion 15, the operation portion 12, and the universal cord 13, to be extended to an endoscope connector (not shown).

As shown in FIG. 1, the operation portion 12 is provided with a first switch 12a and a second switch 12b. The first switch 12a is a lens position switching switch. The first switch 12a outputs an instruction signal for switching the arranging position of the movable lens 52 between a distal end position which is on the distal end lens 51 side and a proximal end position which is opposite to the distal end position.

The second switch 12b is a anti-fogging switch. The second switch 12b outputs an instruction signal for heating the distal end lens 51 to prevent occurrence of fogging on the distal end lens 51.

A first switch cable 7 is extended from the first switch 12a, and a second switch cable 8 is extended from the second switch 12b. The switch cables 7, 8 are inserted through the operation portion 12 and the universal cord 13, to be extended to the endoscope connector (not shown).

The processor 2 is provided with a control circuit 2a. The control circuit 2a is provided with a movable lens control section 2b, a temperature detection section 2c, a heat generation control section 2d, an image processing circuit (not shown), etc.

With reference to FIGS. 2 to 5C, description will be made on the configuration of the distal end side of the insertion portion 11.

Figure 2:
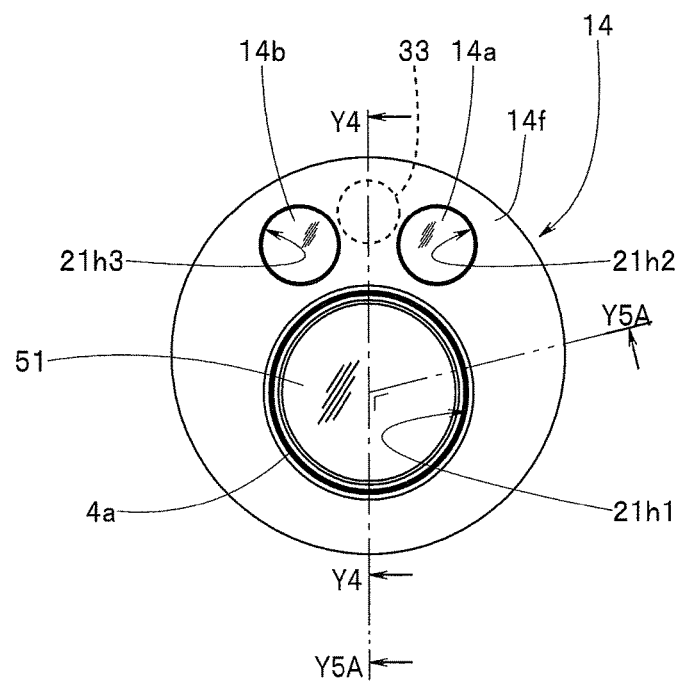
FIG. 2 is a front view of a distal end portion that configures an insertion portion of the endoscope.

As shown in FIG. 2, the distal end lens 51 and a pair of illumination lenses 14a, 14b are provided on a distal end surface 14f of the distal end portion 14, for example.

Figure 4:
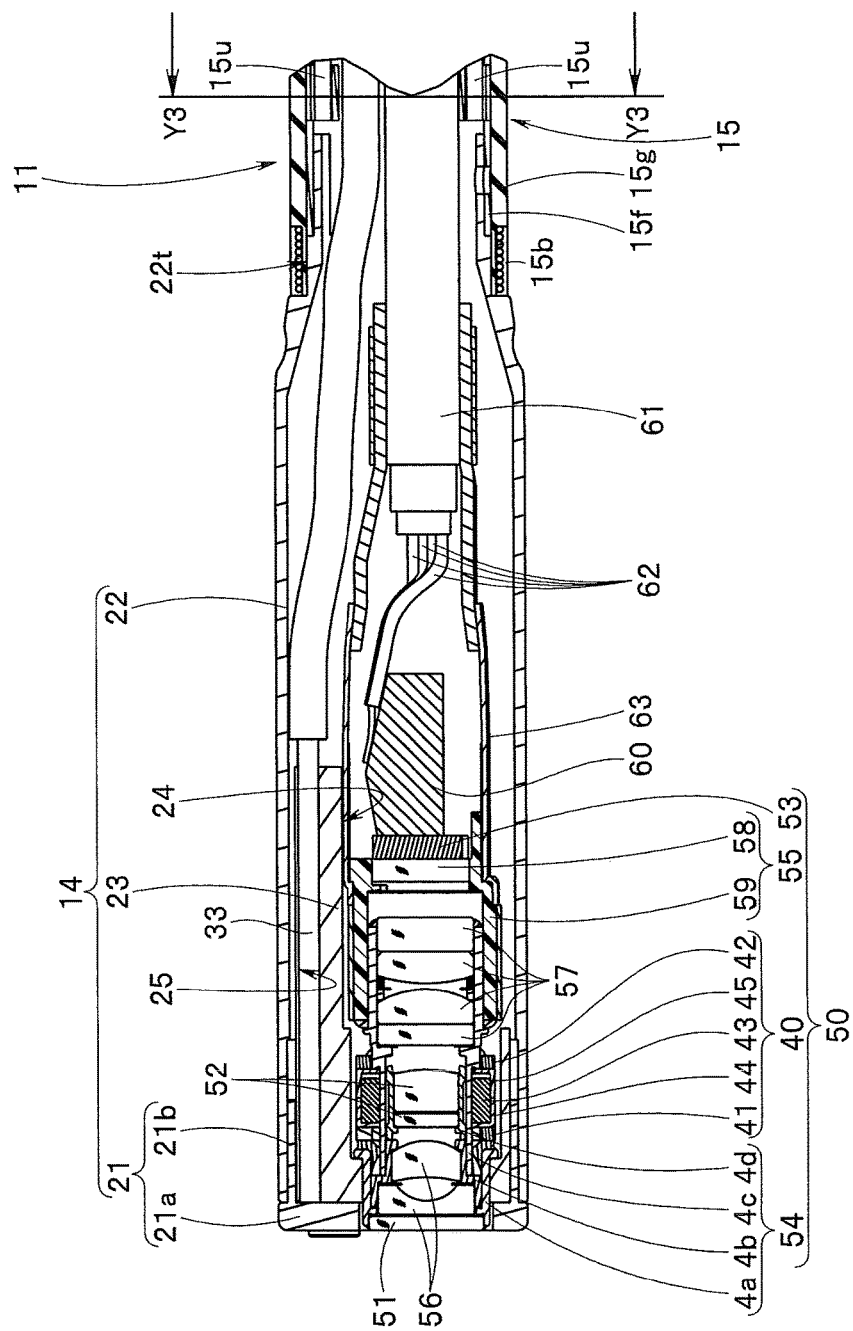
FIG. 4 is a cross-sectional view taken along arrow line Y4-Y4 in FIG. 2.

The bending portion 15 as shown in FIGS. 3 and 4 is provided on the proximal end side of the distal end portion 14 which configures the insertion portion 11.

The distal end portion 14 includes a substantially cylindrical-shaped first distal end barrel member 21, a tubular second distal end barrel member 22, and a columnar-shaped distal end constituting member 23, which are formed in an integrated manner.

The first distal end barrel member 21 and the second distal end barrel member 22 are made of stainless steel, for example. On the other hand, the distal end constituting member 23 is made of, for example, a copper having heat conductivity higher than that of the stainless steel, in view of the heat conductive performance.

The first distal end barrel member 21 includes a main body portion 21a and a ring-shaped portion 21b. One surface of the main body portion 21a configures the distal end surface 14f of the distal end portion 14. The ring-shaped portion 21b is projected from another surface side of the main body portion 21a by a predefined dimension. The outer diameter dimension of the ring-shaped portion 21b is set to be smaller than the outer diameter dimension of the main body portion 21a by a predefined dimension.

As shown in FIG. 2, the main body portion 21a includes through holes 21h1, 21h2, and 21h3 formed thereon. The central axis of each of the through holes 21h1, 21h2, and 21h3 is arranged parallel to the longitudinal axis of the insertion portion. The first objective lens barrel 4a is disposed in the first through hole 21h1. The first illumination lens 14a is disposed in the second through hole 21h2. The second illumination lens 14b is disposed in the third through hole 21h3.

As shown in FIG. 4, the second distal end barrel member 22 configures the outer surface of the distal end portion 14. The inner circumferential surface of the second distal end barrel member 22 is fixed to the outer circumferential surface of the ring-shaped portion 21*b*. At least the outer diameter dimension of the distal end side of the second distal end barrel member 22 fixed to the ring-shaped portion 21*b* is substantially equal to the outer diameter dimension of the main body portion 21*a*.

The second distal end barrel member 22 includes on the proximal end side thereof a thin-diameter portion 22*t*. A distal end portion of a distal end bending piece 15*f* which configures the bending portion 15 is fixed to the thin-diameter portion 22*t*. The distal end portions of bending wires 15*u*, 15*d*, 15*r*, 15*l* as shown in FIGS. 3 and 4 are fixed to predefined positions on the inner circumferential surface of the distal end bending piece 15*f*.

The outer circumferential side of a bending piece group 15C constituted of a plurality of continuously formed bending pieces (not shown) including the distal end bending piece 15*f* is covered with a mesh tube (not shown) and a bending rubber 15*g*. The end portion of the bending rubber 15*g* includes a thread-wound adhering portion 15*b*, to be fixed to a thin-diameter portion 21*t*.

The distal end constituting member 23 includes a through hole for image pickup unit 24, a through hole for heat dissipation line 25, a through hole for first light guide, not shown, and a through hole for second light guide, not shown. The central axis of each of the through holes is parallel to the longitudinal axis of the insertion portion.

Figure 5B:
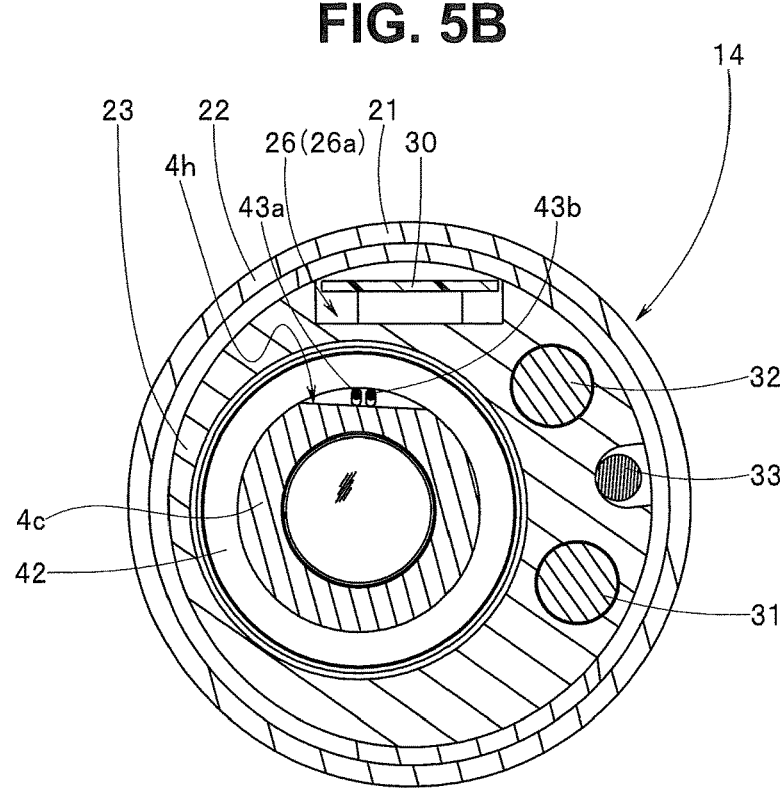
FIG. 5B is a cross-sectional view taken along arrow line Y5B-Y5B in FIG. 5A.

In addition, the distal end constituting member 23 includes a cutout groove 26 as shown in FIGS. 5A and 5B. The cutout groove 26 includes a substrate housing groove 26*a* which is elongated along the longitudinal axis direction of the insertion portion, and a thermistor disposing recessed portion 26*b*. The thermistor disposing recessed portion 26*b* is provided at the distal end portion of the substrate housing groove 26*a*.

The flexible substrate 30 is arranged so as to be housed in the substrate housing groove 26*a*.

The flexible substrate 30 is provided with a contact for thermistor, a contact for coil connection, terminals for wiring, and a wiring section for connecting the respective contacts and the respective terminals, which are not shown.

The thermistor 5 is arranged in the thermistor disposing recessed portion 26*b* for detecting the temperature of the distal end lens 51. The thermistor 5 is connected to the contact for thermistor provided on the distal end side of the flexible substrate 30. A temperature detection surface 5*f* of the thermistor 5 closely contacts with the bottom surface of the thermistor disposing recessed portion 26*b*.

A plurality of terminals for wiring are provided on the proximal end side of the flexible substrate 30. The respective terminals for wiring are connected with the distal end portions of the wirings for sensor 6*a*, 6*b* inserted through the actuator cable 6 and the distal end portions of the dual-purpose wirings 6*c*, 6*d* inserted through the actuator cable 6.

The detected value obtained by the thermistor 5 is outputted to the temperature detection section 2*c* of the control circuit 2*a* through the flexible substrate 30 and the wirings for sensor 6*a*, 6*b*.

In addition, the flexible substrate 30 is electrically connected with the dual-purpose coil 43. The output from the movable lens control section 2*b* of the control circuit 2*a* is supplied to the dual-purpose coil 43 through the dual-purpose wirings 6*c*, 6*d*, the flexible substrate 30, and the like.

A first light guide fiber bundle (reference sign 31 in FIG. 3) that faces the first illumination lens 14*a* is inserted in the through hole for the first light guide. A second light guide fiber bundle (reference sign 32 in FIG. 3) that faces the second illumination lens 14*b* is inserted in the through hole for the second light guide.

In the through hole for heat dissipation line 25 as shown in FIG. 4, the distal end portion of a heat dissipation line 33 is arranged. The heat dissipation line 33 is a heat dissipation member and set to a predefined length dimension. The heat dissipation line 33 dissipates heat, which is generated by the light guide fiber bundles 31, 32 in the distal end portion 14, toward the direction of the proximal end side of the insertion portion 11. The distal end portion of the heat dissipation line 33 is disposed between the first illumination lens 14*a* and the second illumination lens 14*b* (see the dashed line in FIG. 2).

The heat dissipation line 33 is formed by bundling a plurality of wires having high heat conductivity such as a thin copper wire, aluminum wire, silver wire, or the like, in view of both heat capacity and workability. The diameter dimension of the heat dissipation line 33 is appropriately set by taking the inner diameter dimension of the insertion portion 11, the outer diameter dimensions, positions, and the like of the internal components of the endoscope inserted through the insertion portion 11 into consideration.

Note that the reference sign 61 denotes an image pickup cable extended from the image pickup unit 50. A plurality of signal lines 62 are inserted through the image pickup cable 61.

The image pickup unit 50 is disposed in the through hole for image pickup unit 24.

The image pickup unit 50 includes an image pickup device 53, an objective optical system unit 54, an image pickup optical system unit 55, and an actuator unit 40, as shown in FIG. 4 and FIG. 5A. The objective optical system unit 54 includes an objective lens barrel 4 configured by the first objective lens barrel 4*a*, the second objective lens barrel 4*b*, and the third objective lens barrel 4*c*, which are formed in predefined shapes, and the movable lens barrel 4*d*.

The distal end lens 51 is fixed to the inner circumferential surface of the distal end side of the first objective lens barrel 4*a*. The outer circumferential surface of the distal end side of the second objective lens barrel 4*b* is fitted and fixed to the inner circumferential surface of the proximal end side of the first objective lens barrel 4*a*.

A plurality of optical lenses 56 and the like are fixed to the inner circumferential surface of the second objective lens barrel 4*b*. The inner circumferential surface of the distal end side of the third objective lens barrel 4*c* is fitted and fixed to the outer circumferential surface of the proximal end side of the second objective lens barrel 4*b*.

A plurality of optical lenses 57 and the like are fixed to the inner circumferential surface of the proximal end side of the third objective lens barrel 4*c*. The outer circumferential surface of the movable lens barrel 4*d* is movably held on the inner circumferential surface of the distal end side of the third objective lens barrel 4*c*. The movable lens 52 is fixed to the inner circumferential surface of the movable lens barrel 4*d*.

In the present embodiment, the first objective lens barrel 4*a* and the second objective lens barrel 4*b* are heat conductive members, and made of metal members having high heat conductivity, for example, brass, stainless steel, or the like.

The third objective lens barrel 4*c* is a heat conductive member. In addition, the third objective lens barrel 4*c* is provided with the actuator unit 40. Therefore, the third objective lens barrel 4*c* is made of a metal member, for example, brass, stainless steel, or the like which has high heat conductivity and is non-magnetic material, in order not to interfere with the magnetic force for driving the movable lens barrel 4*d* which is generated from the actuator unit 40, and in order to efficiently transmit the magnetic force generated from the actuator unit 40 to the movable lens barrel 4*d*.

The heat from the actuator unit 40 is conducted from the third objective lens barrel 4*c* to the second objective lens barrel 4*b*, and further conducted from the second objective lens barrel 4*b* to the distal end lens 51 via the first objective lens barrel 4*a*.

The movable lens barrel 4*d* is arranged slidably on the distal end inner circumferential surface in the inner hole of the third objective lens barrel 4*c*. Upon receiving the magnetic force from the actuator unit 40, the movable lens barrel 4*d* moves. The movable lens barrel 4*d* is made of, for example, carbon steel or magnetic steel which is a magnetic material.

The image pickup optical system unit 55 is configured by a cover glass 58 being fixed to an image pickup barrel 59. The image pickup device 53 is fixed on the proximal end side of the image pickup barrel 59, with the cover glass 58 interposed. The image pickup barrel 59 is a member having an insulation property and low heat conductivity, and made of ceramic or resin, for example.

The image pickup barrel 59 reduces a bad influence on the image pickup device 53 due to static electricity propagated from outside through the first objective lens barrel 4*a*, the second objective lens barrel 4*b*, and the third objective lens barrel 4*c*, and a bad influence on the image pickup device 53 due to the heat from the actuator unit 40.

The image pickup device 53 is electrically connected to a circuit substrate 60. The circuit substrate 60 is connected with a plurality of signal lines 62. The plurality of signal lines 62 are gathered into one bundle as an image pickup cable 61, inserted through the insertion portion 11, the operation portion 12, and the universal cord 13, and extended to the endoscope connector.

The reference sign 70 denotes a shield barrel. The shield barrel 70 covers and protects the image pickup device 53. The inner circumference on the distal end side of the shield barrel 70 is fitted and fixed to the outer circumference on the proximal end side of the image pickup barrel 59.

The reference numeral 63 denotes an image pickup unit exterior barrel that covers the image pickup unit. The image pickup unit exterior barrel 63 is a heat-shrinkable tube that is shrunk by heat, for example. Sealing resin is filled in the image pickup unit exterior barrel 63. That is, the portion around the image pickup device 53, the circuit substrate 60 and the cable 61 is covered with the sealing resin.

The image pickup barrel 59 is then fixed to the third objective lens barrel 4*c*. As a result, the image pickup unit 50 is configured.

With reference to FIG. 4, FIGS. 5A-5B, description will be made on the configuration of the actuator unit 40.

As shown in FIG. 4 and FIG. 5A, the actuator unit 40 includes a first permanent magnet 41, a second permanent magnet 42, the dual-purpose coil 43, a first yoke 44, and a second yoke 45.

The first permanent magnet 41 and the second permanent magnet 42 are arranged in the optical axis direction, so as to adjacent to the side surface of the first yoke 44 and the side surface of the second yoke 45, respectively, so as to sandwich the dual-purpose coil 43 therebetween in the central axis direction of the image pickup unit 50.

The third objective lens barrel 4*c* includes, at a predefined position on the outer circumference thereof, an outer circumference stepped portion for unit (hereinafter shortly referred to as stepped portion) 4*g*, which is a stepped portion projected outside from a distal end outer circumference 4*e*. The third objective lens barrel 4*c* includes, at a predefined position on the inner circumference thereof, a proximal end side abutting portion 4*r*, which is a circumferential projection portion that projects in the central axis direction of the image pickup unit 50. The movable lens barrel 4*d* is held at a second holding position by the proximal end surface thereof contacting the proximal end side abutting portion 4*r* which is a second position restricting portion when the movable lens barrel 4*d* retreats in the optical axis direction.

The actuator unit 40 is provided on the outer circumference of the third objective lens barrel 4*c*. A conductive wire is wound around the circumference of the distal end outer circumference 4*e*, to form the dual-purpose coil 43.

Note that, in the present embodiment, the conductive wire for forming the dual-purpose coil 43 is directly wound around the outer circumference of the third objective lens barrel 4*c*. However, the dual-purpose coil 43 is not limited to this configuration. The dual-purpose coil 43 may be configured by a conductive wire being indirectly wound around the outer circumference of the third objective lens barrel 4*c*, with an insulation member interposed therebetween, for example.

The yokes 44, 45 are disposed around the dual-purpose coil 43 so as to cover the dual-purpose coil 43. The second yoke 45 is provided so as to abut the stepped portion 4*g* in the optical axis direction, i.e., the central axis direction of the image pickup unit 50. The first yoke 44 is provided so as to abut the second yoke 45.

The yokes 44, 45 are made of, for example, carbon steel or magnetic steel which is a magnetic material, and configured to cover the dual-purpose coil 43 in order to efficiently transmit the magnetic force generated by the dual-purpose coil 43 to the movable lens barrel 4*d*.

Note that, in the present embodiment, the yokes 44, 45 are provided so as to cover the dual-purpose coil 43. However, the yokes 44, 45 may be formed in a cylindrical shape, and provided respectively on the circumference of the distal end outer circumference 4*e* at a position between the dual-purpose coil 43 and the first permanent magnet 41 and at a position between the dual-purpose coil 43 and the second permanent magnet 42, in the optical axis direction, i.e., the central axis direction of the image pickup unit 50.

Alternatively, the yokes 44, 45 may be provided in the optical axis direction, i.e., the central axis direction of the image pickup unit 50 so as to be respectively adjacent to the outside of the first permanent magnet 41 and the outside of the second permanent magnet 42. If the dual-purpose coil 43 is capable of generating a magnetic force sufficient for moving the movable lens barrel 4*d*, it is not necessary to provide the yokes 44, 45.

The cylindrical first permanent magnet 41 is fixed adjacent to the first yoke 44 so as to be located on the distal end side with respect to the first yoke 44 in the optical axis direction, i.e., the central axis direction of the image pickup unit 50. The cylindrical second permanent magnet 42 is fixed adjacent to the second yoke 45 so as to be located on the proximal end side with respect to the second yoke 45 in the optical axis direction, i.e., the central axis direction of the image pickup unit 50. The second permanent magnet 42 is held by the inner circumference thereof being fitted to the outer circumference of the third objective lens barrel 4*c* at a position on the proximal end side with respect to the stepped portion 4*g*.

The first permanent magnet 41 and the second permanent magnet 42 preferably have the same size in order to substantially equalize the influence of the magnetic forces from the permanent magnets on the movable lens barrel 4d. In addition, in order to make the inner circumferential diameter of the first permanent magnet 41 substantially equal to the inner circumferential diameter of the second permanent magnet 42, the first permanent magnet 41 is fixed to the distal end outer circumference 4e with a spacer 46 made of a non-magnetic material interposed therebetween.

In the present embodiment, the spacer 46 is provided in order to make the inner circumferential diameter of the first permanent magnet 41 substantially equal to that of the second permanent magnet 42. However, instead of providing the spacer 46, a protrusion having the same shape as that of the spacer 46 may be formed at the third objective lens barrel 4c.

In this fixed state of the permanent magnets, the N-pole of the first permanent magnet 41 faces the N-pole of the second permanent magnet 42, for example.

Note that, in the present embodiment, the first permanent magnet 41 and the second permanent magnet 42 are disposed such that the polarities (S/N) of the first permanent magnet 41 and the second permanent magnet 42 are set in the moving direction of the movable lens barrel 4d and the opposed surfaces of the first permanent magnet 41 and the second permanent magnet 42 have the same polarity.

Figure 5C:
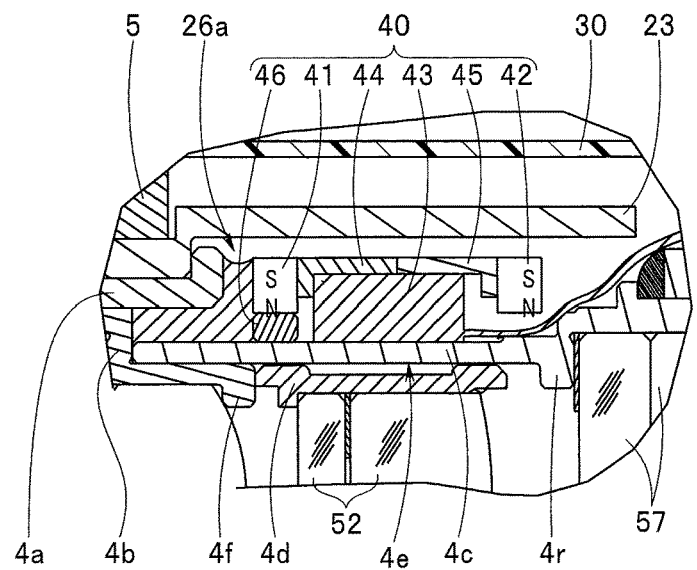
FIG. 5C is an enlarged view of a part indicated with the arrow Y5C in FIG. 5A.

However, the disposition of the permanent magnets is not limited to the above-described one. For example, as shown in FIG. 5C, the first permanent magnet 41 and the second permanent magnet 42 may be disposed such that the polarities (S/N) of the first permanent magnet 41 and the second permanent magnet 42 are set in the direction perpendicular to the moving direction of the movable lens barrel 4d, and the polarities positioned on the movable lens barrel 4d side are the same in the first permanent magnet 41 and the second permanent magnet 42.

In addition, the permanent magnets 41, 42 have cylindrical shapes in the present embodiment. However, the permanent magnets 41, 42 may be divided respectively into plural pieces and disposed on the distal end outer circumference 4e, for example.

Thus, in the optical axis direction, i.e., the central axis direction of the image pickup unit 50, the second yoke 45 is abutted against the stepped portion 4g, and the first yoke 44 and the first permanent magnet 41 are abutted, in this order, against the distal end side of the second yoke 45 and fixed thereto, and the second permanent magnet 42 is abutted against the proximal end side of the second yoke 45 and fixed thereto.

Thus, it is possible to accurately set the mutual positions of the first permanent magnet 41, the first yoke 44, the second yoke 45, and the second permanent magnet 42 in the optical axis direction, i.e., the central axis direction of the image pickup unit 50.

As shown in FIG. 5A, the dual-purpose coil 43, which is formed by winding the conductive wire made of, for example, a copper wire having conductivity around the distal end outer circumference 4e plural times, is provided between the S-pole end surface of the first permanent magnet 41 and the S-pole end surface of the second permanent magnet 42.

One end portion 43a of the conductive wire constituting the dual-purpose coil 43 is connected to one of coil connecting terminals of the flexible substrate 30 and the other end portion 43b is connected to the other of coil connecting terminals of the flexible substrate 30. As a result, the dual-purpose coil 43 and the control circuit 2a are connected to each other through the one end portion 43a and the other end portion 43b of the conductive wire, the flexible substrate 30 and the dual-purpose wirings 6c, 6d.

In order to connect the one end portion 43a and the other end portion 43b of the conductive wire constituting the dual-purpose coil 43 to the flexible substrate 30, a cutout 4h is provided at a predefined position on the outer circumference of the third objective lens barrel 4c, as shown in FIG. 5B. The one end portion 43a and the other end portion 43b of the conductive wire penetrate through a clearance formed by the inner circumference of the second permanent magnet 42 and the cutout 4h of the third objective lens barrel 4c, to be connected to the coil connecting terminals of the flexible substrate 30.

The reference sign 4f denotes a distal end side abutting portion which is a first position restricting portion. The distal end surface of the movable lens barrel 4d abuts the distal end side abutting portion 4f, when the movable lens barrel 4d moves forward. The movable lens barrel 4d abuts the distal end side abutting portion 4f to be held at a first holding position. The distal end side abutting portion 4f is a part projecting in the direction perpendicular to the central axis of the third objective lens barrel 4c, and is the proximal end portion of the second objective lens barrel 4b, for example.

That is, the proximal end portion of the second objective lens barrel 4b projects from the inner hole surface of the third objective lens barrel 4c in a circumferential shape, to form the projection portion. As a result, the movable range of the movable lens barrel 4d in the optical axis direction is defined by the distal end side abutting portion 4f and the proximal end side abutting portion 4r.

In this configuration, the mutual positions of the second objective lens barrel 4b provided with the distal end side abutting portion 4f and the third objective lens barrel 4c provided with the proximal end side abutting portion 4r in the optical axis direction, i.e., the central axis direction of the image pickup unit 50 are determined by the distal end surface of the third objective lens barrel 4c abutting the second objective lens barrel 4b. This enables the positions of the distal end side abutting portion 4f and the proximal end side abutting portion 4r to be defined with high accuracy. As a result, the movable range of the movable lens barrel 4d in the optical axis direction can be set with high accuracy.

Note that, in the present embodiment, the distal end side abutting portion 4f against which the movable lens barrel 4d is abutted is provided at the second lens barrel 4b and the proximal end side abutting portion 4r is provided at the third objective lens barrel 4c, respectively. However, the present invention is not limited to this configuration. A dedicated abutting member provided with one of the above-described abutting portions may be provided, for example. Alternatively, for example, a member provided with one of the above-described abutting portions may be provided such that the position in the optical axis direction of the member is adjustable, to thereby enable the movable range of the movable lens barrel 4d to be adjusted.

The reference sign 23S in FIG. 5A denotes a heat insulating space.

The heat insulating space 23S is a heat insulating layer that prevents heat generated from the dual-purpose coil 43 from being conducted to the distal end constituting member 23. Note that the heat insulating layer is an air layer in the present embodiment. However, a resin having low heat conductivity may be filled in the heat insulating layer, for example.

The reference sign 4j denotes a filler. In the present embodiment, the filler 4j is filled in a part surrounded by the first objective lens barrel 4a, the second objective lens barrel 4b, the third objective lens barrel 4c, and the first permanent magnet 41. The filler 4j is a heat transmitting layer that guides the heat, which has been generated from the dual-purpose coil 43 and conducted to the third objective lens barrel 4c, to the optical lens 56 and the distal end lens 51.

Hereinafter, description will be made on the working of the endoscope system 1.

A mechanism for advancing or retreating the movable lens barrel 4d in the optical axis direction will be described.

In the endoscope system 1 according to the present invention, the image pickup unit 50 of the endoscope 10 is configured to obtain an endoscopic image of a wide range when the movable lens barrel 4d is abutted against the distal end side abutting portion 4f, and obtain an endoscope image of a narrow range when the movable lens barrel 4d is abutted against the proximal end side abutting portion 4r, for example.

The image pickup unit 50 is set such that the movable lens barrel 4d abuts the distal end side abutting portion 4f to obtain an endoscopic image of a wide range, when the power supply of the endoscope 10 is turned on.

Therefore, voltage E1 is applied to cause the movable lens barrel 4d to abut the distal end side abutting portion 4f and to be held at the first holding position, for example. The voltage E1 is a first voltage, which is a minimum necessary voltage to be applied from the movable lens control section 2b to the dual-purpose coil 43 for causing the movable lens barrel 4d to abut the distal end side abutting portion 4f and to be held, or which is a voltage larger than the minimum necessary voltage.

The current outputted from the movable lens control section 2b is supplied, in the following order, to the first dual-purpose wiring 6c, the one end portion 43a of the conductive wire, the dual-purpose coil 43, the other end portion 43b of the conductive wire, and the second dual-purpose wiring 6d.

As a result, the magnetic field of the second permanent magnet 42 is canceled out by the magnetic field of the dual-purpose coil 43, and the magnetic field of the dual-purpose coil 43, the magnetic field of the first permanent magnet 41, and the movable lens barrel 4d are magnetically coupled with one another, and thereby the movable lens barrel 4d is held at the first holding position where the movable lens barrel 4d abuts the distal end side abutting portion 4f. On the other hand, when an operator observes a diseased part, that is, obtains an endoscopic image of a narrow range, the operator operates the first switch 12a provided at the operation portion 12. Then, an instruction signal for switching the position of the movable lens barrel 4d is outputted from the first switch 12a to the processor 2.

Upon receiving the instruction signal, the control circuit 2a supplies current from the movable lens control section 2b in a direction different from the above-described direction, for holding the movable lens barrel 4d at a second holding position where the movable lens barrel 4d abuts the proximal end side abutting portion 4r, to apply the voltage E1 as the first voltage which is the minimum necessary voltage or larger than the minimum necessary voltage to the dual-purpose coil 43, for example. In this case, the current is supplied from the movable lens control section 2b, in the following order, to the second dual-purpose wiring 6b, the other end portion 43b of the conductive wire, the dual-purpose coil 43, the one end portion 43a of the conductive wire, and the first dual-purpose wiring 6c.

As a result, the magnetic field of the first permanent magnet 41 is canceled out by the magnetic field of the dual-purpose coil 43, and the magnetic field of the dual-purpose coil 43, the magnetic field of the second permanent magnet 42, and the movable lens barrel 4d are magnetically coupled with one another, and thereby the movable lens barrel 4d is held at the second holding position where the movable lens 4d abuts the proximal end side abutting portion 4r.

Figure 6:
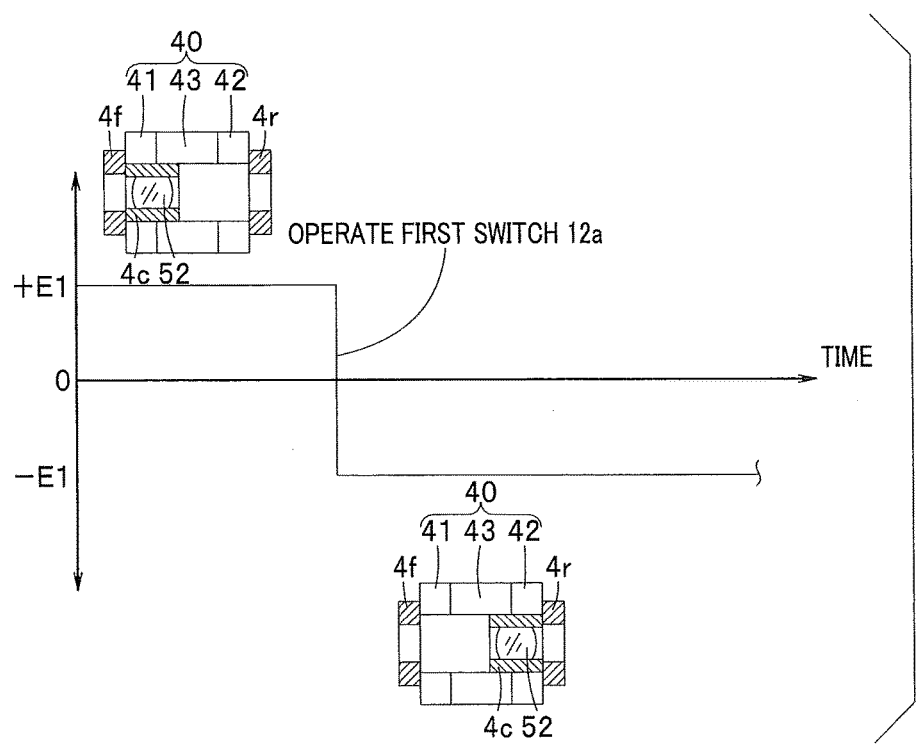
FIG. 6 is a view for illustrating a relation between a voltage and a flowing direction of a current at a time when the voltage is applied to a dual-purpose coil to hold a movable lens barrel with the movable lens barrel abutting an abutting portion.

When the current is supplied to the first dual-purpose wiring 6c, the one end portion 43a of the conductive wire, the dual purpose coil 43, the other end portion 43b of the conductive wire and the second dual-purpose wiring 6d, in this order, the voltage to be applied to the dual-purpose coil 43 is supposed to be +E1, and when the current is supplied to the second dual-purpose wiring 6d, the other end portion 43b of the conductive wire, the dual-purpose coil 43, the one end portion 43a of the conductive wire, and the first dual purpose wiring 6c, in this order, the voltage to be applied to the dual-purpose coil 43 is supposed to be −E1. The relation between the moving direction of the movable lens barrel 4d and the flowing direction of the current can be shown as illustrated in FIG. 6. That is, the absolute value of the voltage to be applied to the dual-purpose coil 43 is the same.

When the operator operates the first switch 12a of the operation portion 12 for obtaining an endoscopic image of a wide range again, the control circuit 2a, upon receiving the instruction signal from the first switch 12a, supplies the current from the movable lens control section 2b in the direction different from the above-described direction, to apply the voltage +E1 to the dual-purpose coil 43.

As a result, the movable lens barrel 4d moves from the second holding position, to be held again at the first holding position where the movable lens barrel 4d abuts the distal end side abutting portion 4f.

Note that the first voltage (E1 or −E1) to be supplied to the dual-purpose coil 43 is sufficient for holding the movable lens barrel 4d at the first holding position or the second holding position. Therefore, when the movable lens barrel 4d is moved from the first holding position to the second holding position, or vice versa, a voltage having an absolute value larger than that of the first voltage (E1 or −E1) may be applied to the dual-purpose coil 43.

In this case, when the operator operates the first switch 12a of the operation portion 12 to set the observation range of the endoscopic image to a different range, the control circuit 2a, upon receiving the instruction signal from the first switch 12a, performs control to apply from the movable lens control section 2b a voltage having an absolute value larger than that of the first voltage (E1 or −E1) for only a predetermined certain time period required for moving the movable lens barrel 4d.

In addition, in the present embodiment, the absolute value of the first voltage to be applied to the dual-purpose coil 43 is set to the same value (E1) in both of the case where the movable lens barrel 4d is held at the first holding position and the case where the movable lens barrel 4d is held at the second holding position. However, as long as the first voltage is minimum necessary voltage for holding the movable lens barrel 4d at the first holding position or the second holding position, the absolute value of the first voltage to be applied to the dual-purpose coil 43 may be different in the case where the movable lens barrel 4d is held at the first holding position and in the case where the movable lens barrel 4d is held at the second holding position.

Next, with reference to FIG. 5A and FIG. 7, a function for preventing fogging of the distal end lens 51 will be described.

In the endoscope system 1 according to the present invention, the temperature around the distal end lens 51 provided at the distal end portion 14 of the insertion portion 11 of the endoscope 10 is detected by the thermistor 5. The detected value obtained by the thermistor 5 is outputted to the temperature detection section 2c.

The thermistor 5 is set to detect the temperature around the distal end lens 51 at the same time that the power source of the endoscope 10 is turned on.

Note that, when the power source is turned on, the movable lens barrel 4d is held abutting the distal end side abutting portion 4f, as described above.

The operator operates the second switch 12b provided at the operation portion 12 when preventing the occurrence of fogging. Then, the instruction signal for heating the distal end lens 51 is outputted from the second switch 12b to the processor 2.

Note that the action of outputting the instruction signal for heating the distal end lens 51 is not limited to be performed by the operation of the second switch 12b by the operator. For example, the instruction signal may be outputted from the processor 2 for a certain time period when the power source of the processor 2 is turned on.

Upon receiving the instruction signal, the control circuit 2a compares a detected temperature C1 obtained by the thermistor 5 with a lens temperature C0 as a specified value registered in a storing section, not shown, provided in the heat generation control section 2d, and the comparison result is determined by a determination section, not shown.

Figure 7:
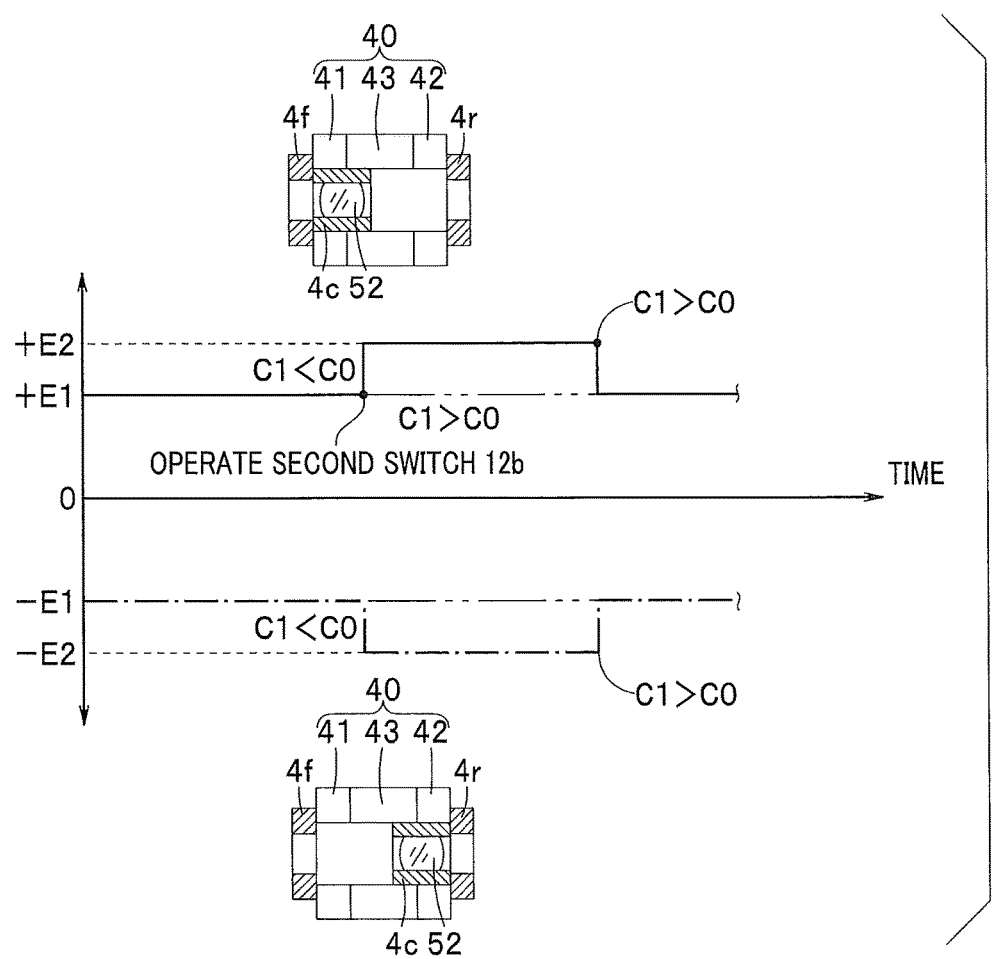
FIG. 7 is a view for illustrating a relation between a comparison result, which is obtained by comparing a detected temperature detected by a thermistor and a temperature specified in advance, and the voltage to be applied to the dual-purpose coil.

When the determination section determines that the detected temperature C1 is higher than the lens temperature C0, the heat generation control section 2d does not perform any control, and as shown in the two-dot chain lines in FIG. 7, the voltage which is being outputted from the movable lens control section 2b is continuously applied to the dual-purpose coil 43.

Note that the lens temperature C0 is set in advance as a temperature at which fogging does not occur on the distal end lens 51 when endoscopic observation is performed.

On the other hand, when the determination section determines that the detected temperature C1 is lower than the lens temperature C0, the heat generation control section 2d outputs to the movable lens control section 2b an instruction signal for applying a voltage having an absolute value larger than that of the voltage which is being outputted from the movable lens control section 2b to the dual-purpose coil 43.

That is, when the movable lens control section 2b applies the voltage +E1 to the dual-purpose coil 43, voltage +E2 as a second voltage which is higher than the voltage +E1 and registered in advance in the storing section, is applied to the dual-purpose coil 43, as shown by the solid line in FIG. 7.

Note that the voltage value registered in the storing section is not limited to the one value +E2, but a plurality of voltage values may be registered in the storing section respectively for temperature differences between the detected temperature C1 and the lens temperature C0.

When the voltage +E2 is applied to the dual-purpose coil 43, the heat generation amount of the dual-purpose coil 43 is increased while maintaining the state where the movable lens barrel 4d abuts the distal end side abutting portion 4f.

As a result, the heat generated from the dual-purpose coil 43 is conducted to the distal end lens 51 and a plurality of optical lenses 56 through the third objective lens barrel 4c, the second objective lens barrel 4b, and the first objective lens barrel 4a, as shown in the arrow in FIG. 5A, which increases the temperature of the distal end lens 51.

When the determination section determines that the detected temperature C1 obtained by the thermistor 5 becomes higher than the lens temperature C0, the heat generation control section 2d outputs to the movable lens control section 2b an instruction signal for applying the previous voltage +E1 (−E1) to the dual-purpose coil 43. Then, the voltage to be applied from the movable lens control section 2b to the dual-purpose coil 43 is switched to the voltage +E1 (−E1).

Note that, the movable lens control section 2b, when applying the voltage −E1 shown with the one-dot chain line to the dual-purpose coil 43, performs control for increasing the temperature of the distal end lens 51 by applying the voltage −E2 as the second voltage to the dual-purpose coil 43.

In the above-described embodiment, the voltage to be applied to the dual-purpose coil 43 is varied. However, the current value may be varied. That is, the electric power to be supplied to the dual-purpose coil 43 is varied, to thereby vary the amount of heat generated from the dual-purpose coil 43.

Note that, in the present embodiment, when the determination section determines that the detected temperature C1 is lower than the lens temperature C0, the heat generation control section 2d outputs to the movable lens control section 2b the instruction signal for applying to the dual-purpose coil 43 the second voltage (E2 or −E2) having the absolute value larger than that of the first voltage (E1 or −E1) which is being outputted from the movable lens control section 2b.

However, if the determination section is not provided and the operator determines that the endoscopic image is affected by fogging, for example, the operator may operate the second switch 12b to cause the movable lens control section 2b to apply the second voltage (E2 or −E2) having the absolute value larger than that of the first voltage (E1 or −E1) to the dual-purpose coil 43 for a predetermined certain period. In such a configuration, the thermistor 5 may not be provided.

In addition, in the present embodiment, the absolute value of the second voltage to be applied to the dual-purpose coil 43 for removing fogging is set to the same value both in the case where the movable lens barrel 4d is held at the first holding position and the case where the movable lens barrel 4d is held at the second position. However, as long as the second voltage is voltage required for removing the fogging, the absolute value of the second voltage to be applied to the dual-purpose coil 43 may be different in the state where the movable lens barrel 4d is held at the first holding position or in the state where the movable lens barrel 4d is held at the second holding position.

Figure 8A:
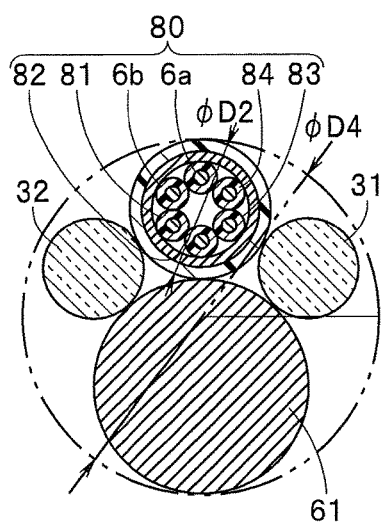
FIG. 8A is a view for illustrating a difference between inner diameters of insertion portions each of which is constituted of an actuator cable having a different configuration and an image pickup cable.
Figure 8B:
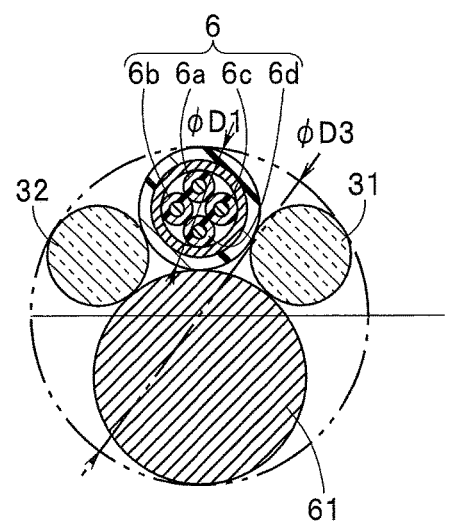
FIG. 8B is a view for illustrating a difference between inner diameters of insertion portions each of which is constituted of an actuator cable having a different configuration and an image pickup cable.

The dual-purpose coil 43 which serves both as the coil as lens driving means and the coil which is a heater as heat generation means is provided in the above-described configuration. Therefore, there is no need for inserting six lines, that is, the wirings for heater 81, 82 and the wirings for driving 84, 85 in addition to the wirings for temperature sensor 6a, 6b in the actuator cable 80 as shown in the configuration in FIG. 8A. That is, as shown in FIG. 8B, the wirings for temperature sensor 6a, 6b and the dual-purpose wirings 6c, 6d are inserted in the actuator cable 6, and two wirings, i.e., the wirings for heaters or the wirings for driving are eliminated.

Therefore, the outer diameter φD1 of the actuator cable 6 is smaller than the outer diameter φD2 of the actuator cable 80. Accordingly, the inner diameter φD3 of the insertion portion through which the actuator cable 6 and the image pickup cable 61 are inserted can be made smaller than the inner diameter φD4 of the insertion portion through which the actuator cable 80 and the image pickup cable 61 are inserted.

As a result, size increase in the outer diameter dimension of the insertion portion 11 is prevented, and connecting operation performance can be also improved by reducing two wirings.

Furthermore, in the above-described embodiment, the dual-purpose coil 43 is provided in the distal end outer circumference 4e of the third objective lens barrel 4c, which eliminates a need for separately providing the lens driving means and the heat generation means at the distal end portion and enables a size decrease in the diameter of the distal end portion.

In addition, a member that constitutes one of the lens driving means and the heat generation means is eliminated from the distal end portion, which enables a space for disposing the thermistor 5 as the temperature detection means to be easily ensured in the vicinity of the distal end lens 51.

The first objective lens barrel 4a, the second objective lens barrel 4b, and the third objective lens barrel 4c are made of metal members having high heat conductivity, and the image pickup barrel 59 is made of, for example, a ceramic resin having heat conductivity lower than that of the three objective lens barrels 4a, 4b, and 4c.

According to such a configuration, the heat generated from the dual-purpose coil 43 can be efficiently conducted to the distal end lens 51 through the third objective lens barrel 4c, the second objective lens barrel 4b, and the first objective lens barrel 4a, without conducting the heat to the image pickup barrel 59. Furthermore, the heat generated from the dual-purpose coil 43 can be prevented from being conducted to the image pickup device 53.

As a result, it is possible to surely prevent the occurrence of fogging on the surface of the distal end lens 51 of the image pickup unit 50 configured to be able to change the optical characteristics or surely remove the fogging occurred on the surface of the distal end lens 51, without increasing the diameter size of the insertion portion 11 of the endoscope 10.

Note that, in the above-described embodiment, the thermistor 5 is arranged in the vicinity of the distal end lens 51 and configured to indirectly detect the temperature of the distal end lens 51. However, the arranging position of the temperature detection means such as the thermistor is not limited to the inside of the thermistor disposing recessed portion 26b formed at the distal end constituting member 23.

For example, instead of the thermistor disposing recessed portion 26b, a through hole for thermistor, which is perpendicular to the optical axis, may be formed at the distal end constituting member 23, to bring the temperature detection surface 5f of the thermistor 5 into closely contact with the first objective lens barrel 4a.

In addition, a groove which is parallel to the optical axis and has an opening portion which opens at the through hole for thermistor may be formed at the first objective lens barrel 4a, to bring the temperature detection surface 5f of the thermistor 5 into directly contact with the distal end lens 51.

In addition, in the present embodiment, the heat generated from the dual-purpose coil 43 is conducted to the distal end lens 51 through the three objective lens barrels 4a, 4b, and 4c, i.e., the first objective lens barrel 4a, the second objective lens barrel 4b, and the third objective lens barrel 4c which constitute the objective lens barrel 4. However, the objective lens barrel 4 may be formed by integrating at least two of the first objective lens barrel 4a, the second objective lens barrel 4b and the third objective lens barrel 4c.

Alternatively, the objective lens barrel 4 may be formed by dividing at least one of the first objective lens barrel 4a, the second objective lens barrel 4b and the third objective lens barrel 4c.

In these cases, the distal end lens 51 is provided at any of or one of the objective lens barrels and the actuator unit 40 is provided on the outer circumference of any of or one of the objective lens barrels.

Figure 10:
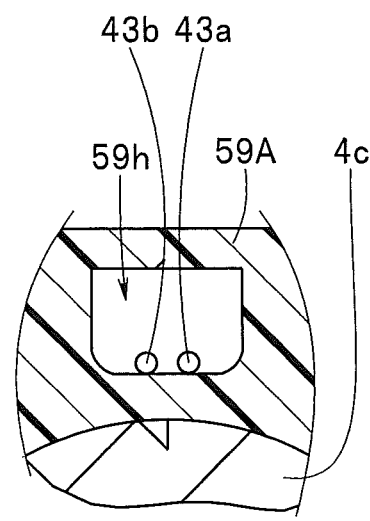
FIG. 10 is a cross-sectional view taken along arrow line Y10-Y10 in FIG. 9.

Another exemplary configuration of the image pickup unit will be described with reference to FIGS. 9 and 10.

In the above-described embodiment, the image pickup unit 50 is configured to connect the one end portion 43a and the other end portion 43b of the conductive wire which constitutes the dual-purpose coil 43 to the flexible substrate 30 arranged outside the image pickup unit 50. The thermistor 5 is mounted to the one end side of the flexible substrate 30.

In the present embodiment, the one end portion 43a and the other end portion 43b of the conductive wire which constitutes the dual-purpose coil 43 are housed in the image pickup unit 50, which eliminates the operation for connecting the one end portion 43a and the other end portion 43b of the conductive wire to the flexible substrate positioned outside the image pickup unit 50, to improve the assemblability.

Specifically, as shown in FIG. 9, the image pickup unit 50A includes an image pickup device 53, an objective optical system unit 54A, an image pickup optical system unit 55A, and an actuator unit 40A.

In the present embodiment, a hole for conductive wire 59h is provided on an image pickup barrel 59A which constitutes the image pickup optical system unit 55A. The one end portion 43a and the other end portion 43b of the conductive wire which constitutes the dual-purpose coil 43 are guided into the image pickup unit exterior barrel 63 through the hole for conductive wire 59h.

In addition, inside the image pickup unit exterior barrel 63, the flexible substrate 30A is disposed. The flexible substrate 30A is provided with coil connecting terminals to which the one end portion 43a and the other end portion 43b of the conductive wire are connected, respectively.

The one end portion 43a and the other end portion 43b of the conductive wire are connected respectively to the coil connecting terminals provided on the flexible substrate 30A.

Thus, the flexible substrate 30A is disposed inside the image pickup unit exterior barrel 63, and the image pickup barrel 59A is provided with the hole for conductive wire 59h for guiding the one end portion 43a and the other end portion 43b of the conductive wire which constitutes the dual-purpose coil 43 into the image pickup unit exterior barrel 63. Then, the one end portion 43a and the other end portion 43b of the conductive wire, which are guided to the image pickup unit exterior barrel 63, are respectively connected to the coil connecting terminals of the flexible substrate 30A.

As a result, connection between the dual-purpose coil 43 and the dual-purpose wirings 6c, 6d are possible without increasing the diameter size of the distal end portion 14.

Note that the one end portion 43a and the other end portion 43b of the conductive wire are connected respectively to the coil connecting terminals of the flexible substrate 30A in the above-described embodiment. However, coil connecting terminals to which the one end portion 43a and the other end portion 43b of the conductive wire are respectively connected may be provided on the circuit substrate 60, without disposing the flexible substrate 30A.

That is, in the present embodiment, the circuit substrate 60 may be configured to serve also as the flexible substrate 30A.

Note that, in the objective optical system unit 54A, a chamfered portion 4ac for filling an adhesive 90 is provided on a proximal end side of a first objective lens barrel 4a1. The adhesive 90 reduces the entry of moisture into the image pickup optical system unit 55A.

In addition, in the objective optical system unit 54A, both of a first permanent magnet 41A and a second permanent magnet 42A are fitted to the distal end side outer circumference of the third objective lens barrel 4c. This enables the spacer 46 for making the inner diameter of the first permanent magnet 41A equal to the inner diameter of the second permanent magnet 42A to be eliminated from the actuator unit 40A.

Note that, in the present embodiment, a cutout 45Ac is provided to a second yoke 45A arranged on the proximal end side of the actuator unit 40A, for allowing the end portions 43a, 43b of the conductive wire which constitutes the dual-purpose coil 43 to extend outside of the actuator unit 40A.

In addition, in order to equalize the influence of the magnetic force from the first yoke 44A on the movable lens barrel 4d and the influence of the magnetic force from the second yoke 45A on the movable lens barrel 4c, a similar cutout 44Ac is provided also to the first yoke 44A which is arranged on the distal end side of the actuator unit, to form the first yoke 44A in a shape same as that of the second yoke 45A.

In addition, there is no need for providing a coil as lens driving means in an image pickup unit which does not include the movable lens barrel 4d for changing the optical characteristics. The image pickup unit in which the lens driving means is not necessary is capable of preventing the occurrence of fogging on the distal end lens or removing the fogging occurred on the distal end lens by providing the heat generation means as shown in FIG. 11A and FIG. 11B.

Figure 11A:
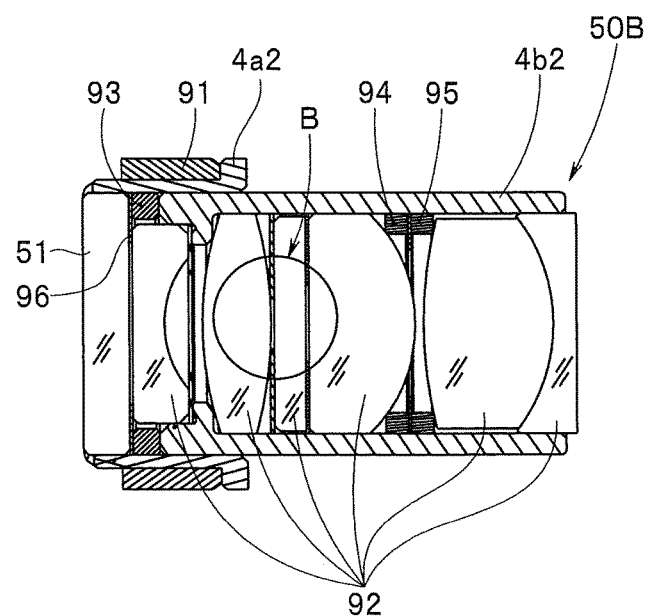
FIG. 11A is a view for illustrating the image pickup unit provided with a coil that generates an electromagnetic wave on an outer circumferential surface of a first objective lens barrel that fixes a distal end lens and a first spacing ring and a second objective lens barrel that are made of a magnetic material.
Figure 11B:
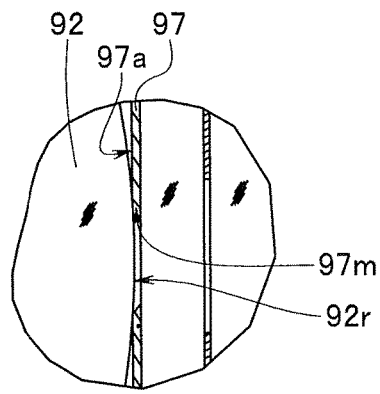
FIG. 11B is a view for illustrating the image pickup unit provided with a coil that generates an electromagnetic wave on an outer circumferential surface of a first objective lens barrel that fixes a distal end lens and a first spacing ring and a second objective lens barrel that are made of a magnetic material.

In the present embodiment, as shown in FIG. 11A, a coil 91 for generating electromagnetic waves is provided on the outer circumferential surface of a first objective lens barrel 4a2 at which the distal end lens 51 constituting the image pickup unit 50B is fixed. The first objective lens barrel 4a2 is made of stainless steel which is a non-magnetic material.

A second objective lens barrel 4b2 to which a plurality of optical lenses 92, and a plurality of spacing rings 93, 94, and 95 are fixed is fixed to the proximal end side inner circumferential surface of the first objective lens barrel 4a2. The first spacing ring 93 is fixed to the distal end surface of the second objective lens barrel 4b1. The distal end surface of the first spacing ring 93 is arranged so as to closely contact with a diaphragm 96 disposed on the proximal end surface side of the distal end lens 51.

The second objective lens barrel 4b2 and the first spacing ring 93 are made of, for example, carbon steel which is a magnetic material, and the second spacing ring 94 and the third spacing ring 95 are made of, for example, stainless steel which is a non-magnetic material.

Note that the image pickup barrel 59 made of ceramic resin to which the image pickup device 53 is fixed with the cover glass 58 interposed is fixed to the proximal end side of the second objective lens barrel 4b2 similarly as in the above-described embodiment, though illustration thereof is omitted.

According to the image pickup unit 50B provided with the coil 91 that generates electromagnetic waves on the outer circumferential surface of the first objective lens barrel 4a2, electromagnetic waves are generated by applying current to the coil 91, to thereby cause the first spacing ring 93 and the second objective lens barrel 4b2, which are made of a magnetic material and arranged in the vicinity of the coil 91, to generate heat. Then, the heat generated by the first spacing ring 93 and the heat generated by the second objective lens barrel 4b2 are conducted to the distal end lens 51 through the diaphragm 96, which increases the temperature of the lens 51. As a result, occurrence of fogging is prevented or the occurred fogging is removed.

A diaphragm 97 illustrated in an enlarged view of the B section shown in FIG. 11B includes an opening 97m formed by etching. Since the opening 97m of the diaphragm 97 is formed by etching, the diaphragm 97 can be manufactured to be thin with high accuracy. In addition, a curved surface 92r side of the optical lens 92 is arranged on a sagged face 97a side (large-diameter side of the opening) formed by etching.

This enables the curved surface 92r of the optical lens 92 to stably abut the sagged surface 97a of the diaphragm 97.

Note that the present invention is not limited only to the above-described embodiments, and various modifications are possible in a range without departing from the gist of the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
   a first lens, a part of which is exposed outside of an endoscope;
   a second lens disposed on a proximal end side with respect to the first lens;
   a first barrel that holds the second lens;
   a second barrel that holds the first lens on a distal end side of an inner circumferential surface of the second barrel, and movably holds the first barrel on a proximal end side of the inner circumferential surface;
   a coil that is wound on an outer circumferential surface of the second barrel, generates a magnetic field for moving the first barrel, and generates heat for heating the first lens; and
   a third barrel that surrounds the second barrel and the coil,
   wherein an inner circumferential surface of the third barrel on a distal end side thereof and the outer circumferential surface of the second barrel are fitted to each other, and
   a heat insulating space for preventing transmission of the heat from the coil to the third barrel is formed between the inner circumferential surface of the third barrel and an entire outer circumferential surface of the coil.

2. The endoscope system according to claim 1, further comprising:
   a temperature sensor that is arranged at a predetermined position on an outer circumferential surface of the third barrel and detects heat,
   wherein the predetermined position is a position opposed to the inner circumferential surface of the third barrel to which the second barrel is fitted, and
   the temperature sensor detects a temperature of the first lens through the third barrel.

3. The endoscope system according to claim 2, further comprising:
- a first abutting portion that is provided at the second barrel and positions the first barrel at a distal holding position on the distal end side,
- a second abutting portion that is provided at the second barrel and positions the first barrel at a proximal holding position on the proximal end side, and
- a control circuit that generates a first voltage and a second voltage higher than the first voltage,
- wherein the control circuit supplies the first voltage to the coil when moving the first barrel to the first abutting portion or the second abutting portion, and supplies the second voltage to the coil when heating the first lens.

4. The endoscope system according to claim 3, further comprising:
- wherein the control circuit, when the temperature detected by the temperature sensor is lower than a predefined temperature, supplies the second voltage to the coil such that the detected temperature becomes equal to or higher than a predetermined temperature.

\* \* \* \* \*